US006464958B1

(12) United States Patent
Bernini et al.

(10) Patent No.: US 6,464,958 B1
(45) Date of Patent: Oct. 15, 2002

(54) PROCESS FOR THE PREPARATION OF SUSPENSIONS OF DRUG PARTICLES FOR INHALATION DELIVERY

(75) Inventors: Eva Bernini, Parma (IT); Chiara Malvolti, Parma (IT); Raffaella Garzia, Parma (IT); Gaetano Brambilla, Parma (IT); Paolo Chiesi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 09/830,884

(22) PCT Filed: Oct. 28, 1999

(86) PCT No.: PCT/EP99/08176

§ 371 (c)(1),
(2), (4) Date: May 22, 2001

(87) PCT Pub. No.: WO00/25746

PCT Pub. Date: May 11, 2000

(30) Foreign Application Priority Data

Nov. 3, 1998 (IT) .......................................... MI98A2364

(51) Int. Cl.[7] ............................. A61K 9/12; A61K 9/10; A61K 31/56
(52) U.S. Cl. ......................... 424/43; 424/45; 424/400; 424/489
(58) Field of Search ........................... 424/400, 43, 45, 424/489

(56) References Cited

U.S. PATENT DOCUMENTS 6,004,566 A * 12/1999 Friedman et al. .......... 424/400

FOREIGN PATENT DOCUMENTS

| EP | 0 416 950 | 3/1991 |
| EP | 0 482 921 | 4/1992 |
| EP | 0 843 998 | 5/1998 |
| WO | WO 93/15741 | 8/1993 |
| WO | WO 99/25359 | 5/1999 |

OTHER PUBLICATIONS

R. Hayes, et al., J. Pharm. Pharmacol., vol. 32, p. 48, "The Effect of Ionising Radiation on Beclomethasone Dipropionate," 1980.
D. M. Bussey, et al., J. Parenter. Sci. Technol., vol. 37, No. 2, pps. 51–54, "Sterilization of Corticosteroids by $^{60}$Co Irradiation," Mar.–Apr. 1983.
A. Denjean, et al., Eur. J. Pediart., vol. 157, pps. 926–931, "Inhaled Salbutamol and Beclomethasone for Preventing Broncho–Pulmonary Dysplasia: A Randomised Double–Blind Study," Oct. 27, 1998.

* cited by examiner

Primary Examiner—Jose' G. Dees
Assistant Examiner—Mina Haghighatian
(74) Attorney, Agent, or Firm—Oblon, Spivak, McClelland, Maier & Neustadt, P.C.

(57) ABSTRACT

The invention is directed to a process for the preparation of suspensions of drug particles for inhalation delivery, said process providing particles of optimized particle size and distribution homogeneously dispersed in the carrier. The process, which is also suitable for the preparation of sterile suspensions, includes the step of homogenizing and micronizing the formulation in a turboemulsifier provided with a high-potency turbine, optionally followed by a treatment in a high-pressure homogenizer. A further aspect of the invention is directed to a process for preparing micronized sterile beclomethasone dipropionate by gamma-irradiation.

20 Claims, No Drawings

PROCESS FOR THE PREPARATION OF SUSPENSIONS OF DRUG PARTICLES FOR INHALATION DELIVERY

The administration of drugs through inhalation has been used for many years and is the mainstay of treatment of diseases which limit airflow, such as asthma and chronic bronchitis.

Furthermore, a number of inhalatory formulations have been marketed for some years, for the administration of steroidal antiinflammatory, decongestant and antiallergic agents for the topical treatment of rhinitis and/or sinusitis.

One of the advantages of the inhalatory route over the systemic one is the possibility of delivering the drug directly at the action site, so avoiding any systemic side-effects. Said way of administration allows to achieve a more rapid clinical response and a higher therapeutic index.

Among the different classes of drugs which are usually administered by inhalation for the treatment of respiratory diseases, glucocorticosteroids such as beclomethasone dipropionate (BDP), dexamethasone, flunisolide, budesonide, fluticasone propionate are of great importance. They can be administered in the form of a finely divided, i.e. micronised, powder, formulated as suspension in an aqueous phase containing any necessary surfactants and/or cosolvents; when intended to be administered in the form of metered doses of aerosol spray, they should also contain a low-boiling propellant.

The effectiveness of the administration form depends on the deposition of an adequate amount of particles at the action site. One of most critical parameters determining the proportion of inhalable drug which will reach the lower respiratory tract of a patient is the size of the particles emerging from the device. In order to ensure an effective penetration into the bronchioli and alveoli and hence ensure a high respirable fraction, the mean aerodynamic diameter (MMAD) of the particles should be lower than 5–6 microns ($\mu$m). For nasal administration, particles with higher MMAD are required.

Other important characteristics for a correct administration and therefore for the therapeutic efficacy, are the size distribution and the homogeneous dispersion of the particles in the suspension.

A poor control of said parameters might favour the formation of loose agglomerates (curds) or, if the curds become compacted and fuse, cakes of suspended particles which, in turn, may impair the possibility of re-suspending the product easily and providing uniform dosing either during the filling of the containers and during the use.

The first object of the present invention is to provide a process for the preparation of particles suspensions for use in pharmaceutical formulations for aerosol inhalation, said particles being characterised by optimised particle size and distribution for obtaining compositions with high therapeutic efficacy.

In a first embodiment of the invention, the process is carried out by using a turboemulsifier, optionally followed by a treatment with a high pressure homogeniser.

Accordingly, said process includes a first step wherein an aqueous solution which constitutes the carrier is dispersed in a turboemulsifier apparatus. A typical turboemulsifier suitable for the treatment comprises a containment vessel equipped with magnetic stirring and a high potency turbine system which is used for homogenising the suspension. The apparatus can also be fitted with a heating steam jacket as well as a vacuum system.

The carrier optionally contains wetting agents, surfactants, viscosity-increasing agents, preservatives, stabilising agents, isotonicity agents and/or buffers and can optionally be sterilised. In a second step, one or more micronised active ingredients, obtained after conventional milling, are added to the aqueous phase and dispersed in the same turboemulsifier vessel by applying very high speed (2000–3000 r.p.m., preferably 2500–2600) for 15–20 min. In has been found that said conditions are necessary in order to effectively disperse the micronised particles of the active ingredient in such a way as to prevent agglomeration during storage. Moreover, it has been more surprisingly found that the particles during said treatment are subjected to a further mild milling which reduces the sizes of the crystals of larger diameter so removing the fractions with higher particle size distribution.

Optionally the process can be carried out under vacuum in order to skim off the suspension.

In a more preferred embodiment of the invention, the drug, dispersed in the aqueous phase, is subjected to an additional homogenisation treatment under high-pressure to further reduce the mean size of the suspended particles. A typical apparatus used for this treatment, such as the Microfluidizer®, includes a high pressure pump which can supply pressures up to 1500 bar and one or more interaction chambers. During the process, the sample is introduced as a stream, then forced at the operating pressure through the interaction chambers where the stream is accelerated to extremely high velocities and subjected to three main forces: i) shear (sliding of particles across one another, tearing); ii) impaction (collisions; crushing); iii) cavitation (collapsing of cavities or bubbles of the surrounding liquid phase; an increased change in velocity with a decreased change in pressure).

The degree of reduction of the solid particles size and the resulting distribution particle curve can be optimised by controlling the following variables i) the type and size of the interaction chamber; ii) the operating pressure; iii) the time of processing and the number of cycle the material is going through.

The effect of the process is also dependent on physicochemical characteristics of the ingredient subjected to the treatment. According to the hardness of its crystalline lattice, different pressure and processing times can be requested to achieve the desired results.

It has now been found that, in case of steroids, it is possible to tighten the distribution particle curve in such a way as that the mean diameter of at least 90% of the particles is lower than or equal to 5 $\mu$m by keeping the operating pressures between 500 and 1000 bar. In particular, particles optimised for pulmonary delivery are obtained using an interaction chamber with sharp edges and maintaining the operating pressure between 600 and 800 bar. Overprocessing at higher pressure should be avoided as it may result in particle-size growth and curds formation. Said surprising results were achieved by submitting the suspension to only one cycle of treatment and therefore for a very short period, making the process very convenient and attractive from an industrial point of view.

The process of the invention is efficiently carried out at room temperature which constitutes a considerable advantage in case of potentially thermolabile molecules such as steroids. On the other hand, the temperature does not significantly increase during the treatment. Furthermore, said specific range of pressures turned out to be suitable for reducing the particle size of the suspended active ingredient without requiring a significant increment in the amount of surfactants. It is general knowledge indeed that the total surface area of the active ingredient increases upon micronisation making sometimes necessary to change the formula of the suspension. Therefore, the breaking of the particles has to be controlled to the degree allowed by the chosen composition.

At the end of the treatment of the invention, particles of particle size distribution within well-defined parameters as well as a good dispersion of the suspended particles are obtained. The resulting formulation is physically stable and it can be easily re-suspended after at least one year of storage.

In order to prevent an increment in the viscosity of the suspension and the formation of even loose aggregates during storage which may puzzle the patient before the use, the process can be preferably carried out by operating at 600–700 bar and by employing an additional interaction chamber arranged in series with respect to the former.

The most widely experienced applications of high-pressure homogenisation regard solid-in-liquid dispersion of paint, pigments, ink-jet printing ink and ceramic powders.

WO 96/14925 deals with dispersion of hard, non-compliant particles used in magnetic recording media such as audio tapes, video tapes or computer diskettes.

Examples of applications to pharmaceutical compositions can be yet found in the prior art but none of them envisages treatment of steroids.

EP 768114 claims the use of said apparatus for treating aerosol formulation containing low-boiling components such as hydrofluoro-carbon alkanes (HFA's) at ambient temperatures. Homogenisation is achieved at 550–620 bar but after repeated cycles of treatment. Micronisation of the active ingredients exemplified i.e. ipratropium bromide and salbuterol sulfate is achieved only at very high pressures (about 1400 bar).

Also EP 726088 claims a process, consisting of re-circulation under high-pressure through multiple tiny openings in order to obtain homogeneously dispersed formulation containing liquefied propellants to be used in pressurised aerosol inhalers.

Illig et al. (Pharm Tech October 1996) in a study aiming at describing the advantages of Microfluidizer® processing over conventional milling treatments, applied such technology to produce suspensions of iodinated radiopaque materials with reduced particle size.

Calvor et al. (Pharm Dev Technol 3, 297–305, 1998) discloses the use of high-pressure homogenisation to produce nanoparticle formulation of polymers (less than 1 $\mu$m and preferably 5–7 nm).

The suspensions prepared according to the process of the invention can be partitioned in suitable containers such as multi-dose or, preferably, single-dose systems for nebulisation, preformed or prepared with the "blow, fill and seal" technology, or pumps or systems for the rhinologic administration.

Both steps, involving respectively the turboemulsifier and the high-pressure homogeniser, can be carried out without any contact with atmosphere and are therefore compatible with working in sterile environment.

All the steps of the process can be carried out on an industrial scale.

The types of dispersion which can preferably benefit of such treatment are: i) sterile suspensions obtained as from a micronised sterile active ingredient; ii) suspensions obtained as from a micronised non-sterile active ingredient.

The process of the invention could also be advantageously utilised for: iii) suspensions obtained from a non-sterile ingredient in the form of non-micronised powder; iv) sterile formulations as a result of wet steam treatment of the bulk suspensions.

In fact, it has been more surprisingly found that particles of the desired particle size distribution can also be obtained by submitting the suspension containing the non-micronised active ingredient to the high-pressure homogenisation treatment. In particular, by applying operating pressures lower than those previously claimed, particles suitable for nasal delivery could be obtained. Said treatment might also be effective in restoring the desired particle size distribution after that unfavourable changes in their profile have occurred as a result of heat-sterilising processes. The latter methods may indeed lead to the formation of aggregates which will hardly de-aggregate into fine particles upon administration.

Drugs which can advantageously be used for preparing the suspensions according to the process of the invention include those steroids which are usually administered by inhalation for the treatment of respiratory diseases, such as beclometasone dipropionate, flunisolide, mometasone furoate, triamcinolone acetonide, dexamethasone, fluticasone propionate, budesonide and its epimers. The corresponding formulations can be prepared by dispersing the active ingredient(s) in an aqueous solution or in high-boiling organic solvents, such as alcohols. According to the particle size and particle distribution obtained, they can be used either for pulmonary or nasal delivery.

Moreover, the particles obtained with the process of the invention, suitably dried, can optionally be conditioned in pressurised dosed areosol inhalers. Suspensions in organic solvents can be directly distributed in containers for pressurised aerosols.

As reported above, the process of the invention is compatible with working under sterile conditions. Since sterility is a requirement more and more demanded for pharmaceutical formulations intended for nebulisation, it would be highly advantageous to provide aqueous suspensions of steroids to be delivered as sterile single-dose preparations. Said formulations allow to avoid the use of antimicrobials or preservatives which are extensively reported to be responsible of allergies and irritations of airways which, in turn, manifest by cough or bronchospasm.

It is therefore a second object of the invention to provide a process for the preparation of particles to be used as aqueous suspensions intended for aerosol inhalation, said particles being constituted of a sterile micronised active ingredient and characterised by an optimal size distribution for obtaining high therapeutic efficacy starting from.

Said process comprises the following steps: i) to prepare an aqueous solution, which constitutes the carrier and optionally containing wetting agents, surfactants, viscosity-increasing agents, stabilising agents, isotonicity agents and/or buffers, in a suitable turboemulsifier vessel; ii) to sterilise the aqueous base inside the same container; iii) to add, in a sterile environment, one or more active sterile micronised ingredients; iv) to disperse all the ingredients by using the same turboemulsifier.

The resulting suspension can be directly partitioned under sterile conditions, in plastic single-dose containers, pre-formed and sterilised by suitable treatments or produced in sterile by employing the "blow, fill and seal" technology.

Before packaging, the suspension can optionally be submitted to a further high-pressure homogenisation treatment, still carried out under sterile conditions.

A third object of the invention is a process for making therapeutically acceptable micronised BDP sterile as a result of gamma-ray irradiation.

The use of gamma irradiation for sterilising steroids has been already reported in the literature. However, data always refer to drugs in the form of powders, solutions, suspensions, creams or ointments; furthermore, even in the most favourable cases, a decrease of the content is often observed which do not conform with the current ICH (International Conference Harmonisation) requirements for pharmaceutical formulations or products intended for.

Hayes R et al. in J Pharm Pharmacol 32 (Suppl), 48P, 1980 compare the stability of powder BDP with respect to that of its solution in methanol or propylene glycol, solvents currently used for the preparation of creams. Cobalt ($^{60}$Co), at doses of 1 to 4 Mrad is used as gamma-irradiating source. The conclusions are that BDP in the form of powder is stable immediately after irradiation while its solutions undergo quick degradation.

Bussey DM et al. in J Parent Sci Technol 37, 51–54, 1983 and Kane MP et al. in J Pharm Sci 72, 30–35, 1983 report data on the degradation of powder corticosteroids sterilised by using $^{60}$Co as irradiating source. The percentage of degradation varies from a minimum of 0.2%/Mrad for prednisone to a maximum of 1.4%/Mrad for hydrocortisone sodium succinate, The degradation following irradiation causes the loss of the C17 side chain and the oxidation of the alcohol group at the C11 position. Sterilisation of micronised steroids was reported in Illum L et al. in Arch Pharm Chemi Sci Ed. 2, 167–74, 1974. The active ingredients submitted to two different radiation doses (4.5 and 15 Mrad) showed different degradation degrees, namely below 1% for hydrocortisone acetate and prednisone and about 2.4% for hydrocortisone, prednisolone and prednisolone hydrate.

WO 99/25359 claims a process for sterilisation of a powdered form of a glucocorticosteroid, preferably budesonide, by employing temperatures (from 100 to 130° C.) significantly lower than those considered necessary for the heat sterilisation of other substances.

PT-A-69652 disclosed cold sterilisation of micronized glucocorticosteroids using mixture of ethylene oxide and carbon dioxide. Specific examples are prednacinolone, dexamethasone, prednisolone and salts, esters and fluoro derivatives thereof. Sterile BDP is not reported. Furthermore, the technique requires the elimination of residual ethylene oxide which is time consuming and difficult. In the light of the present strict regulatory requirement the method would be not suitable for producing therapeutically acceptable glucocorticosteroids.

In summary, methods of sterilisation, in particular gamma-ray irradiation, has never been previously applied to micronised beclomethasone dipropionate (BDP). Moreover, the stability upon storage of the corresponding suspensions of the micronised irradiated product has never been verified. Degradation processes may indeed start after a significant lag-time due to the energy stored up by the drug after irradiation.

It has now surprisingly been found that BDP micronised substance when subjected to gamma-irradiation at 2 to 9 KGy under particular conditions, remains chemically stable. Contrary to what has been reported in WO 99/25359 for budesonide, no significant chemical degradation was observed with respect to the non-irradiated product. Sterile BDP micronised substance according to the process of the invention experiences any change neither in its crystalline characteristics, as demonstrated by DSC (Differential Scanning Calorimetry), TGA (Thermal Gravimetric Analysis), XRD (X-ray diffractometry), IR (infrared spectrum), nor in its particle size as proved by Malvern analysis. Also the corresponding suspensions turned out to be physically and chemically stable after long-term and accelerated storage conditions.

The process is carried out on the product packed in containers made of suitable materials, preferably polythene, after having replaced air by nitrogen, or optionally under vacuum; the containers are, in turn, sealed in bags made of oxygen-proof materials such as Polikem® or Co-pack®.

It has indeed been found that the presence of oxygen during irradiation dramatically affects the stability of the product as the latter becomes more sensitive to oxidative processes. The ratio between the volume of the container and the amount of micronised powder should also be kept as low as possible and necessarily equal or less than 7:1 w/v.

The present process was validated according to the International Standard Organization Procedure ISO-11137-2B in order to ensure a Sterility Assurance Level (SAL) of at least $10^{-6}$ (preferably $10^{-7}$) and it yields a material sterile according the criteria of the European Pharmacopoeia (Ph.Eur).

The method of the invention allows to solve the technical problem of preparing micronised BDP sterile suspensions to be used for nebulisation. Sterilisation methods of the prior art carried out directly on the final formulation are indeed not suitable; aseptic filtration cannot be utilised due to non-filterability of suspended particles, while wet steam (autoclaving) involves a degree of heat which can be only tolerated by thermostable steroids. For instance, BDP suspensions subjected to a wet steam process under conditions similar to those reported in U.S. Pat. No. 3,962,430 (121° C. for 15 minutes) undergo a remarkable decrease in the content in active ingredient (about 8–9%), with a corresponding significant increase in degradation products (about 10–11%).

The BDP starting material for the process has a bioburden of less than 100 CFU (colony forming units) per gram, preferably less tan 10 CFU per gram and is used in the form of micronised powder, particularly in the form of particles having a MMAD of less than 10 $\mu$m, more preferably less than 5 $\mu$m.

The corresponding formulation for inhalation can be advantageously used in the treatment of any allergic condition and/or inflammatory condition of the nose or lungs, such as asthma as well as of bronchopulmonary dysplasia either in hospital and domiciliary setting.

The invention is further illustrated by the following examples.

EXAMPLE 1

Sterilization of Micronized BDP by Gamma-irradiation

About 600 g of micronised BDP was stored in a 20 l polythene container after having replaced air by nitrogen, the container was in turn sealed in two Polikem bag. The product was subjected to gamma-irradiation at 2 to 9 KGy. After the exposure, the BDP purity and the amount of related substances were determined by HPLC. On the batch subjected to 2 kGy dose, the particle size as well as the loss of weight were also determined by Malvern analysis and TGA respectively, in comparison to the non-irradiated product.

All batches were submitted to the sterility test according to direct inoculation method reported in Ph.Eur. Samples of 0.5 g of irradiated powders were inoculated with the following viable ATCC micro-organism: 360 UFC of *Staphylococcus aureus*, 400 UFC of *Bacillus subtilis*, 350 UFC of *Clostridium sporogens*, 330 UFC of *Candida Albicans*. After addition of 1% polysorbate 80, the culture media were incubated for 14 days. The micro-organism population were measured in comparison to the non-irradiated product.

The results are reported in Table 1.

TABLE 1

| Determinations | Non-irr. BDP | Irr. BDP 2 KGy | Irr. BDP 3.17 KGy | Irr. BDP 9.08 KGy |
|---|---|---|---|---|
| Loss of weight (%, TGA) | 0.12 | 0.13 | — | — |
| Purity (%) | 99.7 | 99.6 | 99.6 | 99.3 |
| Related substances (%) | 0.3 | 0.4 | 0.4 | 0.7 |
| Particle size distribution ($\mu$m, Malvern) | | | | |
| d (0.1) | 0.49 | 0.48 | | |
| d (0.5) | 1.91 | 1.81 | | |
| d (0.9) | 5.98 | 5.73 | | |

The results demonstrate the BDP is stable after exposure to gamma-irradiation. Only a slight increase in chemical degradation was observed after exposure to 9.08 KGy. However, the corresponding batch complies to the purity specifications.

The particle size of the batch exposed to 2 KGy was not affected. No water uptake was observed. All batches comply with the sterility requirements of Ph.Eur.

EXAMPLE 2
Preparation of a Sterile Suspension by Means of the Turboemulsifier Starting from Micronised BDP Sterilised by Gamma-radiation at the Dose of 2 Kgy (Example 1)

| | | Composition |
|---|---|---|
| Components | Total | Per pharmaceutical unit |
| Sterile micronised BDP | 40.0 g | (0.8 mg) |
| Polysorbate (Tween) 20 | 100.0 g | (2.0 mg) |
| Sorbitan monolaurate | 20.0 g | (0.4 mg) |
| Sodium chloride | 900.0 g | (18.0 mg) |
| Sterile water for injection q. s. to | 100.0 l | (2.0 ml) |

The preparation of the sterile suspension comprises a first step wherein the aqueous base is prepared inside a turboemulsifier Tecninox 100 L placed under a laminar flow hood, in a controlled-contamination environment. After loading the apparatus with sterile water for injection, sodium chloride and surfactants are added, and the preparation is mixed under magnetic and high-potency turbine stirring to homogeneously disperse the surfactants.

The preparation is then sterilised inside the turboemulsifier, fitted with a heating steam jacket, at 121° C. for about 20 minutes.

After cooling the preparation down to a temperature of 35° C., the sterile active ingredient is added to the sterile aqueous base, still under a laminar flow hood: the active ingredient is dispersed under first only magnetic stirring, then with the aid of the turbine system at 2600 r.p.m for 15–20 minutes.

Afterwards the turboemulsifier is connected through a sterile tube to the reservoir of the distributing apparatus and placed under laminar flow hood in controlled-contamination environment; ally 2.15 ml of the suspension are distributed in each single-dose plypropylene dispenser pre-sterilised by beta-irradiation.

EXAMPLE 3
Particle Size Analysis of the Preparation Obtained According to Example 2

The size distribution of the suspended particles obtained by the process described in example 2 were evaluated by Malvern light-scattering analysis. The parameter monitored is the volume mean diameter ($\mu$m) of 10%, 50% and 90% of the particles, expressed as d(0.1), d(0.5) and d(0.9), respectively, and it is determined assuming that the particles themselves have a geometrical shape equivalent to a sphere.

Samples were analysed after 6 months of storage under accelerated conditions (40° C., 75% relative humidity) and after 6 and 12 months of storage under long-term conditions (25° C., 60% relative humidity). The results are reported in Table 2.

TABLE 2

| Storage Time (months) | Malvern Data | BDP susp. ($\mu$m) |
|---|---|---|
| 0 | d(0.1) | 0.76 |
| | d(0.5) | 3.01 |
| | d(0.9) | 9.42 |
| 6 (40° C., 75% R.H.) | d(0.1) | 0.78 |
| | d(0.5) | 3.05 |
| | d(0.9) | 8.03 |
| 6 (25° C., 60% R.H.) | d(0.1) | 0.79 |
| | d(0.5) | 3.17 |
| | d(0.9) | 9.62 |
| 12 (25° C., 60% R.H.) | d(0.1) | 0.78 |
| | d(0.5) | 3.5 |
| | d(0.9) | 9.78 |

R.H. = relative humidity

The results confirm that suspended BDP micronised particles subjected to gamma-ray radiation, in suspension, keep unchanged their particle size after storage.

EXAMPLE 4
Multi Stage Liquid Impinger Analysis

The nebulisation performances of the sterile suspensions obtained with the process described in example 2 were evaluated by multi-stage liquid impinger (M.S.L.I.) analysis according to the apparatus and the procedure described in USP/NF. Nebulisation was carried out using a commercial nebuliser (Micron-Medel) for 5 minutes. Said test allows to evaluate the respirable dose of the formulation which corresponds to the sum of the fine particle dose (amount of particles having a size lower than 6.8 $\mu$m) and the extra fine particle dose (amount of particles having a size lower than 3 $\mu$m).

The results are reported in Table 3 as a mean of two determinations. Two different preparations obtained according the example 2 were compared to a marketed formulation.

TABLE 3

| Dose ($\mu$g) | Ref. | Prepar. 1 | Prepar. 2 |
|---|---|---|---|
| Fine dose | 30.5 | 104.0 | 128.5 |
| Extra fine dose | 12.0 | 78.0 | 83.0 |

The results show a dramatic improvement of the fine and extra fine doses for the preparations obtained according to Example 2, confirming that the treatment with the turboemulsifier improves the size distribution and dispersibility characteristics of the particles. Furthermore, the results prove that gamma-irradiation does not negatively affect the nebulisation performances.

EXAMPLE 5
Chemical Stability of the Sterile Suspensions Prepared from Gamma-ray Irradiated Micronised BDP The formulations obtained by using the process described in example 2 were distributed in polypropylene single-dose containers previously sterilised by beta-irradiation and tested after storage under accelerated and long-term conditions according to the ICH guide-lines. The results in terms of chemical stability of the active ingredient are reported in Tables 4 and 5. The assay of BDP and its main degradation products (beclomethasone-17-propionate, beclomethasone-21-propionate and beclomethasone) was carried out by HPLC.

TABLE 4

Chemical stability of the formulation stored under accelerated conditions (40° C., 75% R.H.).

| Time (months) | BDP assay (g/100 ml) | Degradation products* (% w/w) | pH |
|---|---|---|---|
| 0 | 0.0388 (100%) | 1) 0.16<br>2) 0.18<br>3) <LOD | 4.7 |
| 3 | 0.0395 (101.8%) | 1) 0.13<br>2) 0.16<br>3) <LOD | 3.7 |
| 6 | 0.0396 (102.1%) | 1) 0.12<br>2) 0.15<br>3) <LOD | 3.7 |

(*) degraded: 1) Beclomethasone-17-propionate; 2) Beclomethasone.-21-propionate; 3) Beclomethasone
LOD: limit of detection; n.d.: not detected.

TABLE 5

Chemical stability of the preparation stored under long-term conditions (25° C., 60% R.H.).

| Time (months) | BDP assay (g/100 ml) | Degradation products* (% w/w) | pH |
|---|---|---|---|
| 0 | 0.0388 (100%) | 1) 0.16<br>2) 0.18<br>3) <LOD | 4.7 |
| 3 | 0.0396 (102.1%) | 1) 0.15<br>2) 0.17<br>3) <LOD | 4.0 |
| 6 | 0.0390 (100.5%) | 1) 0.15<br>2) 0.16<br>3) <LOD | 4.0 |
| 9 | 0.0375 (96.6%) | 1) 0.12<br>2) 0.16<br>3) <LOD | 3.8 |
| 12 | 0.0413 (106.4%) | 1) 0.13<br>2) 0.17<br>3) <LOD | 4.0 |

(*) degraded: 1) Beclomethasone-17-propionate; 2) Beclomethasone.-21-propionate; 3) Beclomethasone
LOD: limit of detection; n.d.: not detected.

The results of Tables 4 and 5 confirm that the characteristics of the formulations prepared with the process of the invention are maintained unchanged after storage under both conditions. Neither a decrease in the content nor an increase in degradation products was observed. The slight decrease in the pH values can be attributed to the lack of buffers in the formulation.

The formulation turned also be sterile according to Ph. Eur.

EXAMPLE 6
Characterisation of the Suspensions Obtained Starting from Non-sterile Micronised BDP and Further Subjected to High-pressure Homogenisation A BDP suspension of the formula reported in example 2 was prepared in a turboemulsifier starting from non-sterile micronised active ingredient. The resulting product was then transferred to the main interaction chamber of the high-pressure homogeniser and submitted to one cycle of treatment at increasing pressures. Particle size and nebulisation performances were determined by Malvern light-scattering and multi-stage liquid impinger analysis, respectively. The results are reported in Tables 6 and 7 in comparison to a suspension not subjected to high-pressure homogenisation.

TABLE 6

Malvern analysis of a BDP Suspension prepared in a 100 l turboemulsifier.

| Pressure | $d(0.1)$ $\mu$m | $d(0.5)$ $\mu$m | $d(0.9)$ $\mu$m |
|---|---|---|---|
| 500 Bar | 0.84 | 3.53 | 8.73 |
| 800 Bar | 0.85 | 2.48 | 5.42 |
| 1000 Bar | 0.82 | 2.43 | 5.07 |
| Ref. | 0.92 | 2.77 | 7.63 |

The analysis of the data shows a reduction of the particle size parameters as well as of the particle distribution range starting from an operating pressure of 500 bar.

TABLE 7

Malvern and M.S.L.I. analysis of a BDP suspension prepared in a 10 l turboemulsifier.

| Pressure | $d(0.1)$ $\mu$m | $d(0.5)$ $\mu$m | $d(0.9)$ $\mu$m | Fine dose $\mu$g | Extra-fine dose $\mu$g |
|---|---|---|---|---|---|
| 590–610 Bar | 0.58 | 1.37 | 2.88 | — | — |
| 700–720 Bar | 0.59 | 1.37 | 2.80 | — | — |
| 800–820 Bar | 0.59 | 1.36 | 2.80 | 160.7 | 112.3 |
| 890–910 Bar | 0.58 | 1.36 | 2.76 | — | — |
| 1000–1020 Bar | 0.57 | 1.34 | 2.72 | — | — |
| Ref. | 0.58 | 2.11 | 6.95 | 89 | 57 |

The suspensions treated with the homogeniser evidence a significant reduction of the particles size and of the size distribution range.

Furthermore, the suspensions treated with the high-pressure homogeniser are characterised by remarkably improved nebulisation performances as demonstrated by the fine and extra fine doses.

EXAMPLE 7
Stability of the Suspensions Obtained Starting from Non-sterile Micronised BDP and Subjected to High-pressure Homogenisation Treatment at 600 Bar A BDP suspension of the following formula was prepared as reported in the example 2 starting from non-sterile micronised active ingredient.

| Components | Composition Total | Per pharmaceutical unit |
|---|---|---|
| Micronised BDP | 40.0 g | (0.8 mg) |
| Polysorbate (Tween) 20 | 100.0 g | (3.0 mg) |
| Sorbitan monolaurate | 20.0 g | (0.4 mg) |
| Sodium chloride | 900.0 g | (18.0 mg) |
| Sterile water for injection q. s. to | 100.0 l | (2.0 ml) |

The suspension was transferred to the main interaction chamber of the high-pressure homogeniser and submitted to one cycle of treatment at 600 bar. The homogeneiser was also fitted with an additional interaction chamber arranged in series with respect to the former. The resulting product was distributed in polypropylene single-dose containers pre-sterilised by beta-irradiation and stored under long-term conditions (25° C., 60 R.H.). The particle size of the suspended particles after 1 year of storage was determined by Malvern light-scattering analysis. The results are reported in Table 8.

TABLE 8

| Storage Time (months) | Malvern Data | BDP susp. (μm) |
|---|---|---|
| 0 | d(0.1) | 0.71 |
| | d(0.5) | 1.96 |
| | d(0.9) | 4.05 |
| 12 | d(0.1) | 0.78 |
| | d(0.5) | 2.02 |
| | d(0.9) | 4.06 |

The particle size do not change during storage confirming the physical stability of the formulation. Furthermore the suspension is easily re-suspended after manual shaking and no formation of even loose aggregates is observed.

EXAMPLE 8

Particle Size Characterisation of the Suspensions Obtained Starting from Non-sterile Non-micronised BDP and Subjected to High-pressure Homogenisation A BDP suspension of the formula reported in example 2 was prepared in a turboemulsifier starting from non-sterile non-micronised active ingredient and subject to the same treatment reported in the example 6. Particle size and nebulisation performances were determined as previously reported.

The results are reported in Table 9.

TABLE 9

| Pressure | d(0.1) μm | d(0.5) μm | d(0.9) μm |
|---|---|---|---|
| 150 Bar | 0.81 | 3.16 | 9.93 |
| 300 Bar | 0.72 | 2.67 | 8.50 |
| 500 Bar | 0.70 | 2.09 | 5.49 |
| Ref. | 1.40 | 16.84 | 108.05 |

The results reported in Table 8 also prove that the high-pressure homogenisation treatment of the suspension prepared by using the non-micronised product remarkably reduces the particle size and tightens the particle distribution range.

What is claimed is:

1. A process for the preparation of an aerosol inhalable suspension of particles, comprising:

a) preparing a suspension of a steroid active ingredient, in a turboemulsifier provided with a turbine adapted for homogenising the suspension;

b) optionally subjecting the resulting suspension to a further treatment in a high pressure homogeniser, thereby forming said aerosol inhalable suspension.

2. A process according to claim 1, wherein:

a) one or more micronised active ingredients are dispersed, with the aid of said turboemulsifier, in an aqueous solution comprising a carrier, optionally sterilised by heating or filtration and optionally containing wetting agents, viscosity-increasing agents, preservatives, stabilising agents, isotonicity agents and/or buffers;

b) the resulting suspension is further subjected to homogenising and micronising in said high-pressure homogeniser;

c) the suspension is partitioned in containers.

3. A process according to claim 1 in which the preparation is carried out under sterile conditions starting from a sterile micronised active ingredient.

4. A process according to claim 1 in which the suspension prepared starting from an active ingredient in the form of non-micronised, non-sterile powder is subjected to the high-pressure homogenisation treatment.

5. A process according to claim 2 wherein said steroid active ingredient is micronised in said high-pressure homogeniser.

6. A process according to claim 5 in which the micronised active ingredient is a corticoid.

7. A process according to claim 5 in which the micronised active ingredient has been sterilised by gamma-ray irradiation.

8. A process according to claim 5 in which the micronised active ingredient is beclomethasone dipropionate.

9. A process according to claim 5 in which the volume diameter of at least 90% of the particles is lower than or equal to 5 μm.

10. A process according to claim 2 where the high-pressure homogenisation treatment occurs at pressures from 500 to 1000 bar.

11. A process according to claim 10 wherein said high-pressure homogenisation treatment occurs at pressures from 600 to 800 bar.

12. A process for the sterilisation of micronised beclomethasome dipropionate which process comprises gamma irradiation at 2 to 9 KGy.

13. The process according to claim 2 wherein the turboemulsifier operates at 2000–3000 r.p.m. and for 15–20 minutes.

14. The process according to claim 2 wherein homogenisation treatment is effected in one cycle of treatment.

15. The process according to claim 10 wherein homogenisation treatment is effected in one cycle of treatment.

16. The process according to claim 11 wherein homogenisation treatment is effected in one cycle of treatment.

17. Therapeutically acceptable micronised beclomethasone dipropionate which has been sterilized by gamma-ray irradiation.

18. The therapeutically acceptable micronised beclomethasone dipropionate according to claim 17 wherein the gamma-ray irradiation is between 2 and 9 kGy.

19. A method of treatment of an allergic condition and/or inflammatory condition of the nose or lungs comprising administering to a patient in need thereof the product according to claim 17.

20. The method according to claim 19 wherein said condition is bronchopulmonary dysplasia.

* * * * *